Figure 1:
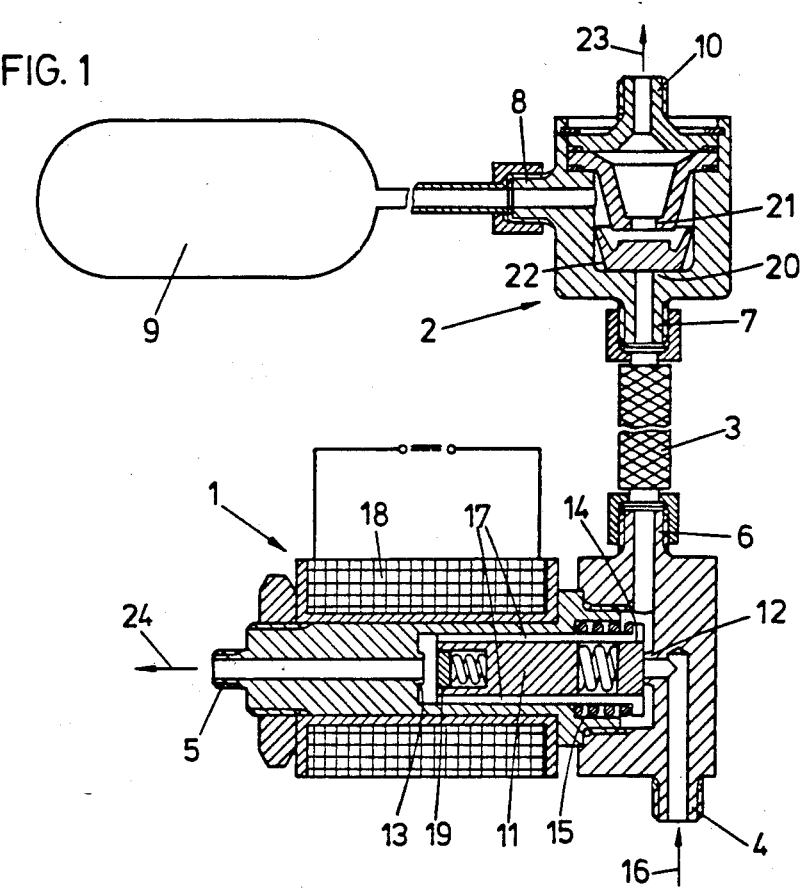

United States Patent [19]

Czech

[11] Patent Number: 4,595,004
[45] Date of Patent: Jun. 17, 1986

[54] APPARATUS FOR THE TREATMENT OF THE LUNGS OF HUMANS OR ANIMALS

[76] Inventor: Kurt Czech, 13, Schwarzenbergplatz, A-1040 Vienna, Austria

[21] Appl. No.: 650,686

[22] Filed: Sep. 17, 1984

[51] Int. Cl.$^4$ ............................................. A61M 16/00
[52] U.S. Cl. .......................... 128/204.21; 128/200.21; 128/205.24
[58] Field of Search ...................... 128/205.24, 204.21, 128/204.24, 204.25, 205.13, 205.19, 200.21

[56] References Cited

U.S. PATENT DOCUMENTS

| | | |
|---|---|---|
| 2,918,917 | 12/1959 | Emerson . |
| 3,610,236 | 10/1971 | Smilg ............................... 128/204.24 |
| 3,672,366 | 6/1972 | Burchell et al. . |
| 3,902,487 | 9/1975 | Okmian . |
| 4,001,700 | 1/1977 | Cook et al. . |
| 4,033,343 | 7/1977 | Jones . |
| 4,121,580 | 10/1978 | Fabish ............................. 128/205.13 |
| 4,318,399 | 3/1982 | Berndtsson ..................... 128/202.22 |
| 4,351,329 | 9/1982 | Ellestad et al. . |
| 4,374,521 | 2/1983 | Nelson et al. ................... 128/205.24 |
| 4,393,869 | 7/1983 | Boyarsky et al. . |
| 4,401,115 | 8/1983 | Monnier ......................... 128/205.13 |
| 4,409,977 | 10/1983 | Bisera et al. . |

*Primary Examiner*—Henry J. Recla
*Attorney, Agent, or Firm*—Spensley Horn Jubas & Lubitz

[57] ABSTRACT

An apparatus is disclosed which is capable of providing pressure shocks of from 1 to 20 Hz at a pressure of 0.1 to 5 bar, to the lungs of a mammal. The apparatus includes a source of pressure gas, a gas supply duct leading from the source to the mammal application site, and a system communicating with the gas supply duct, the system having a selectively actuated valve which can provide gaseous access from the gas source along the gas supply duct and to a second valve, the position of the second valve being controlled by the actuation of the first valve such that the second valve alternately provides access from the gas source to a pressure vessel, and from the pressure vessel to the mammal application site.

11 Claims, 7 Drawing Figures

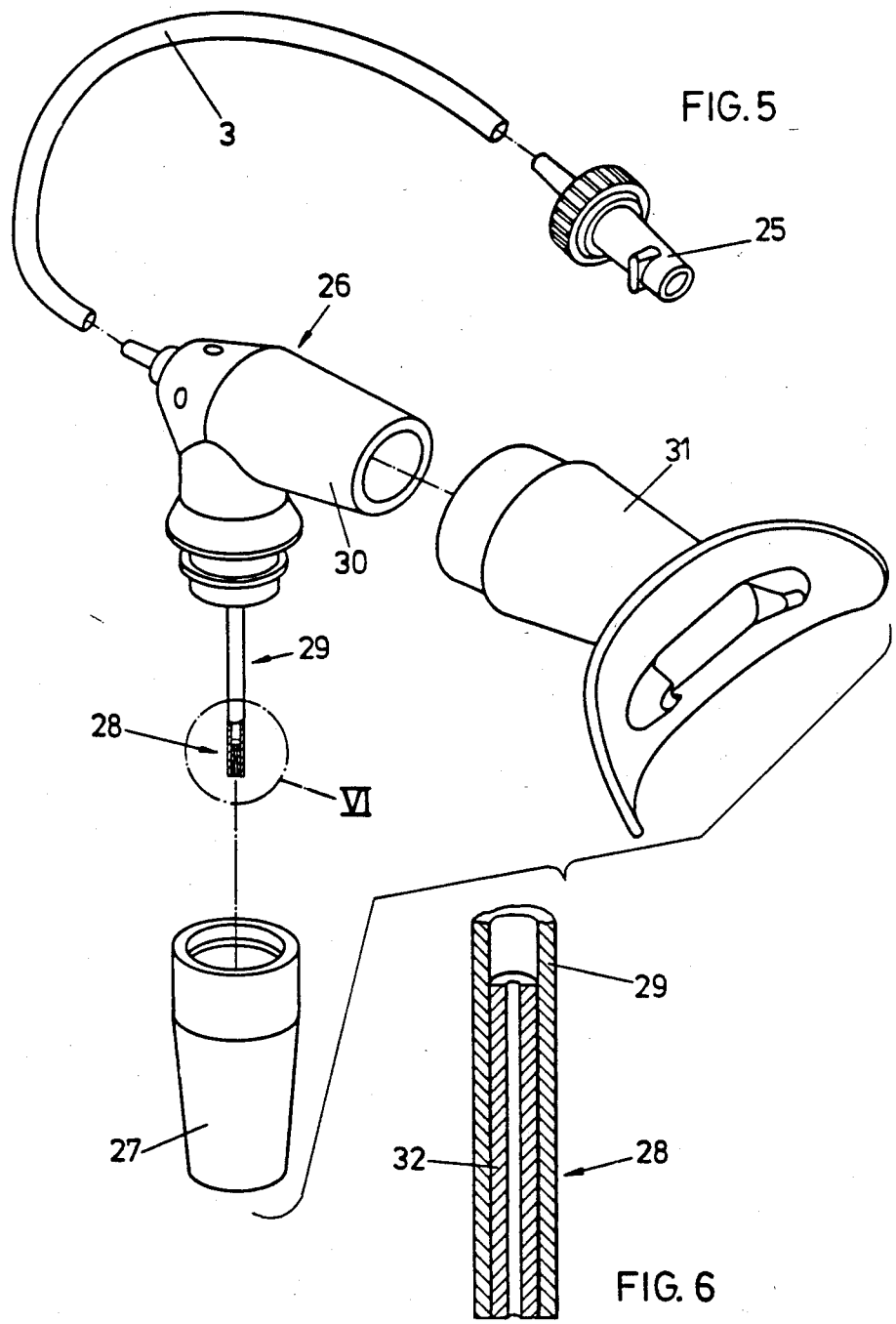

APPARATUS FOR THE TREATMENT OF THE LUNGS OF HUMANS OR ANIMALS

The invention relates to an apparatus for the treatment of the lungs of humans or animals, which apparatus includes a source of pressure gas and a duct leading to the site of application, a valve to be actuated with frequencies of from 1 to 20 Hz being interposed in the duct for forming pressure shocks or pulses in the region of from 0.1 to 5 bars.

Known apparatusses of this kind—so-called jet generators—work with a 2/2-way valve, i.e. a valve that has two connections and two switching positions, i.e. a simple opener-closer. As valves, various closing organs, such as solenoid valves, pneumatic valves, or pneumatically pre-controlled solenoid valves have been utilized.

These apparatusses are used for artifical respiration or for the therapeutic treatment of accumulations of secretion in the space of the lungs or the bronchi.

In many cases of application it has proven particularly suitable to superpose the pressure shocks produced by such an apparatus, which last for about 50 to 200 ms, to the spontaneous respiration or an artificial respiration, whereby, e.g., tough, thixotropic accumulations of secretion are liquified and can be coughed off easily. Also the uptake of oxygen by injured pulmonary lobes—for instance, in case of serial rib fractures—can be extraordinarily improved by using these apparatusses.

The site of application may be at an endotracheal tube, the duct may, however, also end in a mouth piece, the cavity of the mouth being the site of application. The apparatusses operate with a comparatively high gas pressure and, in the known embodiments, constitute a risk of hazard, since, during the opening phase of the valve there exists a direct connection between the source of pressure gas and the site of application. If, however, the pressure connection into the lungs or into the trachea, lasts for a longer period of time, even if it lasts for about 1 or 2 s only,—i.e. if the valve gets caught—this may in some instances lead to irreversible barotraumas. Very short pressure shocks, i.e. those in the region of approximately 50 to 200 ms, are harmless for the patient and yield the desired therapeutic effect.

Because of this risk, various efforts have been made to let the valves function more reliably, thus, e.g., not to design a solenoid valve as a spring-loaded valve, but to provide a separate solenoid for each switching position. Furthermore, also rotary slide valves have been considered. Also, pressure control devices arranged following the valves have been proposed.

A further disadvantage of the known apparatusses resides in the rectangular shape of the pressure shocks created by them, due to which relatively large gas volumes flow to the site of application in each opening phase of the valve. If a patient is artificially respirated, these gas volumes may even lead to considerable malfunctions of the respiration appliances.

The invention aims at avoiding the described disadvantages and difficulties and has as its object to provide an apparatus of the initially described kind, which is safer in operation than those previously available, gives a more suitable and more effective pulse form of the pressure shocks and reliably saves the patients from harm.

According to the present invention, the set object is achieved in that an active 3/2-way valve is interposed in the gas duct, and that furthermore, between this valve and the site of application, a passive 3/2-way rapid deaerating valve having a sealing body that is movable to and fro between two valve seats is provided in the duct, which alternately makes a connection between the source of pressure gas and a pressure vessel or between the pressure vessel and the site of application.

With the apparatus according to the invention thus there is never a direct connection between the source of pressure gas and the site of application. The volume of the individual gas shock corresponds maximally to the content of the pressure vessel. In case of a sudden failure of the valves or the cycle control, a volume overcharge of the patient and thus a damage to his lungs due to pressure is impossible.

The pulse shape of the pressure shocks is approximately trapezoidal or triangular, depending on the cycle length. From this there results a low gas amount per individual cycle despite a high peak gas flow, as compared to that gas amount flowing out during a pressure or gas shock of rectangular shape created by conventional apparatusses.

By selecting a suitable flow resistance which is determined by the cross-section and length of the duct portion leading from the passive 3/2-way rapid deaerating valve to the site of application, the triangular or trapezoidal pulse course to a large extent can approach the shape of a sine half-wave. Such a pulse shape otherwise is only attainable by complex and clinically hardly utilizable piston-connecting-rod aggregates.

As the active 3/2-way valve, suitably a solenoid valve having small flow cross-sections and low moved masses is provided, which also with high frequencies can be operated without problems. Basically, also another type of valve, such as an electro-pneumatic valve, may be used as the active valve.

Advantageously, a passive 3/2-way rapid deaerating valve having larger flow cross-sections as compared to the active 3/2-way valve is provided. Since in a passive valve the sealing body has only a low mass, such a valve can follow easily also pressure shocks of higher frequencies despite larger flow cross-sections.

It is a further object of the invention to controllably humidify the brief gas shocks to be introduced at the site of application.

Medical gases need be humidified. This holds particularly true for gases from pressure ducts and pressure bottles in which they must be nearly free from water for technical purposes. The necessary amount of water is in the order of 40 mg/l. Rapid gas flows, like those of jet generators, cannot be humidified according to the conventional methods, such as by passing heated water therethrough, passing them slightly above a heated water surface, or passing them by constructions containing wet wicks.

Humidifying before the valve—i.e. in the region of a slow gas flow—is as such technically possible, yet for reasons of hygiene, because of the growing of germs on humid surfaces, it requires a sterilization of the whole system. A humidification of the gas shocks hitherto has been realized with very complex apparatusses by adding water by means of active dosing means (e.g., roller pumps).

Thus, the problem of humidification hitherto has not been solved satisfactorily.

If a humidifying device working according to the injector principle (perfume atomizer) is used, in which a suction pipe for liquid ends at the mouth of the gas duct, then, if the diameter of the water supply pipe is of approximately equal size as the mouth of the gas duct, too much humidity is entrained and so-to-say a fog is formed, whereas with a suction pipe for liquid whose inner diameter is too narrow, no water is introducible.

According to the invention, this problem is solved with a humidifying device arranged in front of the site of application at the end of the gas supply duct and working according to the injector principle in that the suction pipe has a diameter approximately equal to that of the gas supply duct, which has, however, a throttling site in the region where it enters into the humidifying liquid, in particular a capillary tube sealed relative to the inner wall of the suction pipe.

This humidifying device works self-sucking without necessitating complicated external additional devices, such as peristaltic pumps. By selecting a suitable inner diameter and length of the throttling site, the amount of humidity added to each gas shock can be controlled quite easily. Despite a minimum of construction expenditures the humidifying device works with a precision sufficient for clinical purposes. The decisive advantage resides in the handiness and simple sterilizability of this supplementary device.

According to a preferred embodiment of the apparatus according to the invention a pressure sensor is installed in the pressure vessel, which pressure sensor is electrically conductively connected with the active 3/2-way valve via an electronic controlling element. When the pre-selected nominal pressure has been reached in the pressure vessel, the active 3/2-way valve is switched over by a signal emitted by the pressure sensor, with a solenoid valve, for instance, the current supply to the magnetizing coil of the active valve is interrupted by a current pulse and thus the emptying of the pressure vessel towards the site of application is initiated. Due to the mechanical inertia of the valve, there results a time lag between the pressure detection by the pressure sensor and the effective response of the valves, which in most cases lies in the range of approximately 30 ms. Since the pressure increase in the pressure vessel is not a linear function of the time which is available for filling the vessel, the approximately constant time lag mentioned causes the nominal pressure to be exceeded by various extents, depending on whether the nominal pressure is low or slightly below maximum.

For these reasons, the electronic controlling element preferably includes a microprocessor for the exact regulation of the switch-over time of the active 3/2-way valve taking into consideration the pressure increase varying in dependence on the nominal pressure in the pressure vessel during the constant span of time between the pressure detection by the pressure sensor and the response of the two 3/2-way valves.

As the pressure sensor, in particular a piezo-electric pressure transformer is installed in the pressure vessel.

In clinical practice in many cases it is very desirable to use a gas mixture of precisely defined composition. Mixing devices for obtaining air-oxygen-mixtures, for instance, in medical appliances operate mostly as analogous mixers with adjustable needle nozzles. Such appliances can be built relatively small, yet close to the two extremes (nearly pure oxygen or nearly pure air) they are relatively inaccurate. Since, with an intermittent flow, undefined flow conditions prevail for a short time, such systems furthermore can be used with jet generators only by interposing large buffer vessels of sufficient accuracy.

Conventional mixing devices for respiration appliances depart from the prerequisite that the desired mixing ratio must be maintained in each instant. Although a mixing device with digital mixing is known, which device allows for the maintenance of exact mixing ratios also in the extreme regions mentioned, this mixing device also includes a mixing vessel holding several liters.

For overcoming the deficiencies described, according to a further embodiment of the apparatus according to the invention, a further active 3/2-way valve is provided in the gas supply duct in front of the active 3/2-way valve, seen in the flow direction of the gas, for admixing a second gas and a reducing valve is interposed between the two active 3/2-way valves, each of the two inlets of the further active 3/2-way valve being connected with a source of pressure gas.

According to this embodiment, the individual gas shocks are alternately delivered with the one and with the other gas; therein the cycle ratio is adjusted such that the desired gas mixture results, departing from the knowledge that the lungs always contain a sufficiently large gas volume so as to function themselves as the mixing vessel. With this embodiment it is particularly advantageous that no particular attention need be paid to the height of the pressure of the gases flowing into the further active 3/2-way valve, since the gas pressure is limited to a certain height by means of the reducing valve. The two gases may also be supplied with pressures differing greatly from each other, without negatively affecting the mixing accuracy of the device.

Preferably, the two active 3/2-way valves are electrically interconnected via an electronic controlling member which allows for a switch-over of the further active 3/2-way valve only as long as the first active 3/2-way valve interrupts the gas flow from the reducing valve. A switch-over of the further active 3/2-way valve from one gas to the other one, while the first active 3/2-way valve is still opened for the gas supply from the source of pressure gas, disturbs the function of the passive 3/2-way rapid deaerating valve.

Figure 2:
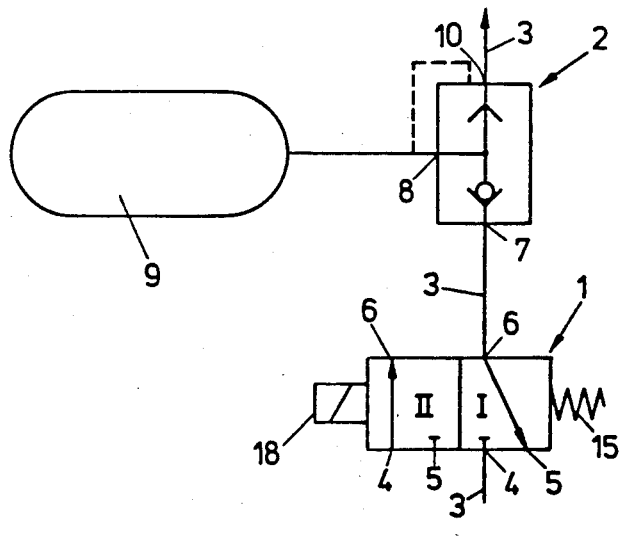
Figure 3:
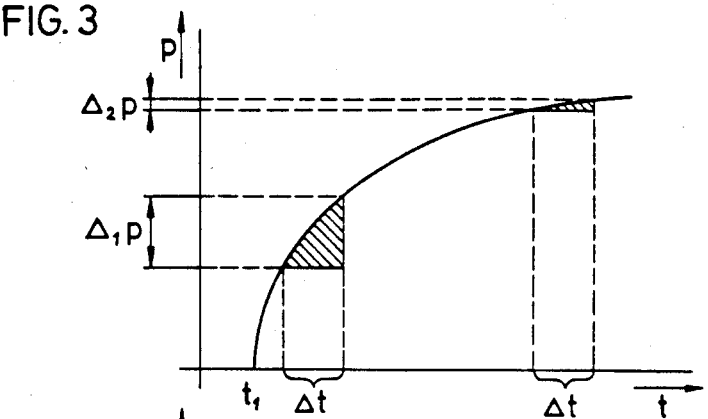
Figure 4:
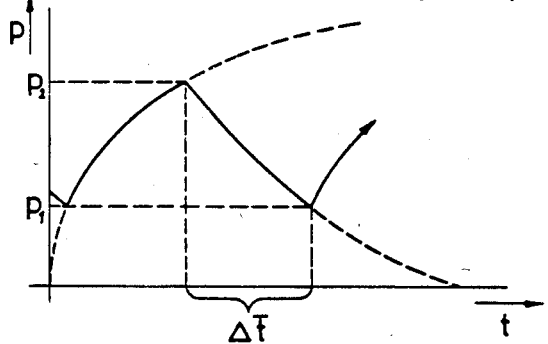
Figure 7:
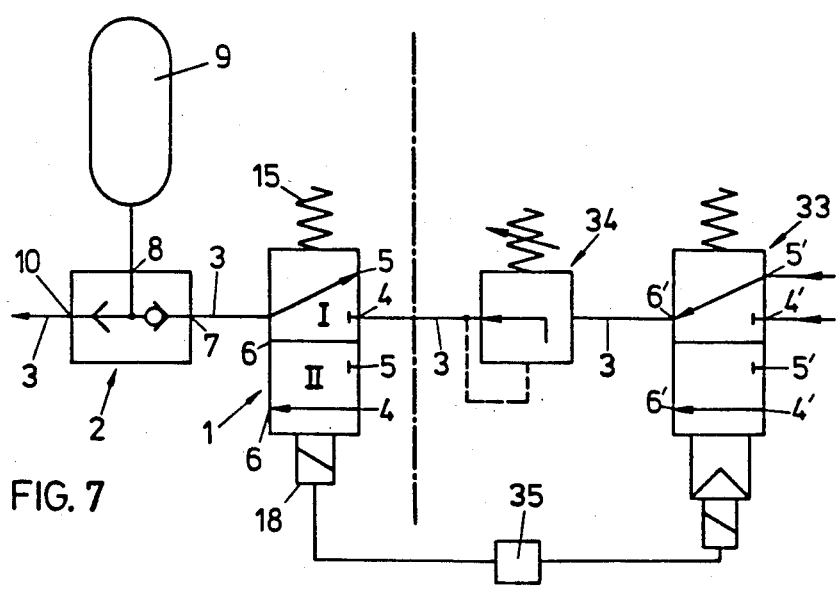

In the following, the invention is explained in more detail by way of the accompanying drawings, wherein FIG. 1 shows schematically an embodiment of the apparatus according to the invention, partly sectioned, with the pressure source and the site of application not shown;

FIG. 2 is a circuit diagram of the apparatus according to FIG. 1, switching symbols according to DIN ISO 12 19 having been inserted for the valves;

in FIG. 3 the pressure course in the pressure vessel in dependence on the time of connection to the source of pressure gas is shown;

from FIG. 4 the actual pressure course in the vessel under an operating condition for forming pressure shocks of higher frequencies can be seen;

in FIG. 5 the individual parts of a humidifying device belonging to the apparatus according to the invention are shown in exploded view including the duct part leading away from the passive 3/2-way valve, and a mouth piece;

FIG. 6 shows a section through an enlarged portion of the mouth region of the liquid suction pipe of the humidifying device according to FIG. 5;

and FIG. 7 is a circuit diagram of an embodiment of the apparatus suitable for admixing a second gas.

An active 3/2-way valve—i.e. a solenoid valve—is generally denoted by 1 in FIG. 1, and a passive 3/2-way rapid deaerating valve is denoted by 2. The valves 1 and 2 are interposed in a duct 3 leading from a source of pressure gas to the application site, in FIG. 1 only the gas duct portion interconnecting the two valves, which may be a metal pipe or a flexible tube of pressure-proof material, being illustrated. The gas duct from the source of pressure gas leads to the connection 4 of the active valve 1. The connection 5 of the valve 1 enters into a vessel maintained under comparatively low pressure or into the surrounding atmospere. The connection 6 of the valve 1 is connected with the connection 7 of the passive valve 2. The second connection site 8 of the valve 2 enters into a pressure vessel 9. The third connection 10 of the passive valve 2 leads to the site of application.

The sealing piston 11 of the valve 1 is movable to and fro between the two valve seats 12 and 13. In a first switching position, the sealing 14 of the sealing piston 11 is pressed against the valve seat 12 under the action of a spring 15, whereby the gas flow coming from the source of pressure gas from the direction of the arrow 16 is interrupted. The connections 5 and 6 of the active valve 1 are simultaneously interconnected via recesses 17 in the sealing piston 11. In the second switching position, i.e. when current flows through the magnetizing coil 18, the sealing 19 of the sealing piston 11 is pressed against the valve seat 13, whereby a flow connection is formed between the connections 4 and 6 of the valve 1 and the connection 5 is blocked.

The sealing body 22 of the passive valve 2, which sealing body is movable to and fro between the valve seats 20 and 21, either forms a connection between the connection 7 of the valve 2—and thus the source of pressure gas—and the connection 8, i.e. the pressure vessel 9, or between the connection 8 and the connection 10, which means between the pressure vessel 9 and the site of application. Arrow 23 indicates the direction of the gas flow to the site of application.

The apparatus works as follows:

As long as the magnetizing coil 18 of the active 3/2-way valve 1 is flowed through by current, gas can flow from the source of pressure gas from direction 16 via the connections 4 and 6 of the valve 1, the portion of the duct 3 connecting the valves 1 and 2, and furthermore via the connections 7 and 8 of the passive 3/2-way rapid deaerating valve 2 into the pressure vessel 9. The sealing body 22 of the valve 2 thus is pressed against valve seat 21. As soon as the current flow through the magnetizing coil 18 has been interrupted, less pressure prevails on the side of the sealing body 22 facing the valve seat 20 than on the other side of the sealing body 22, which other side, via connection 8, is exposed to the inner pressure of the pressure vessel 9 that is filled now, since the valve 1 blocks the connection to the source of pressure gas and the connection 7 of the valve 2 is in connection with the surrounding atmosphere or with the interior of a container under low pressure via the connections 5 and 6 of the valve 1. Accordingly, the sealing body 22 is pressed against the valve seat 20, and the pressure vessel 9 empties via the connections 8 and 10 of the passive valve 2 in the direction 23 to wards the site of application.

With the switch-over process explained of the passive valve 2, also a certain portion of the gas volume stored in the pressure vessel 9 gets lost via the connection 5 of the active valve 1 in the direction 24 due to the inertia of the sealing body 22. This portion may be reduced by measures reducing the outflow speed of the gas from the connection 5—e.g. by providing a cross-section narrowing having a throttle effect.

If the active 3/2-way valve 1 thereupon is opened again for the gas flow from the source of pressure gas by supplying current to the magnetizing coil 18, the valve 2 again is passively switched over, the emptying of the pressure vessel 9 to the site of application is interrupted and a renewed filling phase of the pressure vessel starts.

The switching processes explained above are briefly illustrated in the circuit diagram according to FIG. 2. The switching symbols have been completed as far as possible by reference numerals allocated to corresponding apparatus parts according to FIG. 1. The two switching positions of the active 3/2-way valve 1 are denoted by I and II.

As already mentioned above, the pressure increase in the pressure vessel is not linear. The individual course of the pressure-time-characteristic line depends on the pre-pressure adjusted at the source of pressure gas, on the length and the cross-section of the gas duct, on the flow conditions in the valves, the volume of the pressure vessel 9 as well as on the nominal pressure to be obtained in the pressure vessel; however, the basic shape always corresponds to the diagram shown in FIG. 3 for an individual filling cycle, in which diagram the filling time is plotted on the abscissa and the associated pressure is plotted on the ordinate. The gas supply starts at the time $t_1$. The pressure in the pressure vessel at first increases rapidly, whereafter the curve flattens progressively until the maximum pressure has been reached, which corresponds to the pre-pressure adjusted at the source of pressure gas.

In practice, i.e. when pressure shocks of higher frequencies are delivered by the apparatus, the pressure vessel never reaches the maximum degree of filling, emptying starts already earlier. The pressure vessel is, however, not completely emptied before the next filling cycle starts. The actual pressure course in the pressure vessel, while the apparatus is in operation, can be seen from FIG. 4. The valve switch-over takes place with a constant frequency $1/\Delta t$, and the vessel pressure lies between the limits $p_1$ and $p_2$. The theoretical course of the curve without valve switch-over is indicated in broken lines for the filling and emptying. For adjusting and monitoring a certain desired pressure ($p_2$ in FIG. 4), according to a preferred embodiment a pressure sensor is installed in the pressure vessel 9, which precisely determines the switch-over time of the active 3/2-way valve 1 via an electronic controlling element.

Since, however—as already mentioned at the beginning—there results a varying pressure advance ($\Delta_1 p$ and $\Delta_2 p$ according to FIG. 3) between the pressure detection by the pressure sensor and the actual response of the two 3/2-way valves in dependence on the desired nominal pressure (with a constant time lag $\Delta t$ according to FIG. 3), it is particularly suitable to provide a microprocessor as a component of the electronic controlling element, which microprocessor compensates this pressure characteristic and emits the signal for the switch-over of the active 3/2-way valve 1 already at a pressure value which results from the nominal pressure minus the respective pressure advance $\Delta p$.

For the clinical practice, the valves 1 and 2 including the connecting duct portion as well as the pressure vessel 9 may be installed in a casing, at which casing outer connections for the duct portion coming from the source of pressure gas and for the duct portion leading to the site of application are provided. These connections are, e.g., designed as conical supports for a sealing cone and provided with bayonet closing means. The exposed duct portions suitably are flexible tubes of a synthetic material that is resistant to pure oxygen, such as polyurethane.

In FIG. 5, a flexible duct portion 3 which can be slipped onto a connection cone 25 provided with a bayonet closing means is illustrated. To the other end of the duct portion 3 a humidifying device generally denoted by 26 with a store tank 27 for liquid and working according to the injector principle is connectable. If the store tank 27 is united with the humidifying device 26—in the example illustrated, by slipping on and snapping in—the mouth 28 of the suction pipe 29 immerses into the humidifying liquid contained in the tank 27. Onto the humidifying device 26 also a cone 30 having a larger diameter is shaped, onto which a mouth piece 31 or another suitable connecting piece with intubation hose can be slipped. Immediately at the exit 10 of the valve 2, the pressure shocks still have an approximately triangular shape, which already after about 1 m of duct having an inner diameter of about 3 mm between the valve 2 and the site of application to a large extent approaches the desired sine half-wave.

The mouth 28 of the suction pipe 29 illustrated in FIG. 6 on an enlarged scale has a capillary tube 32 sealed relative to the inner wall of the suction pipe.

In the circuit diagram according to FIG. 7, the construction part on the left-hand side of the dot-and-dash line is identical to that illustrated in FIG. 2.

For admixing a second gas, a further active 3/2-way valve 33 is interposed in the gas supply duct 3, whose inlets 4' and 5' each are connected with a source of pressure gas, e.g. one for oxygen and one for air. Via the connection 6', alternately one of the two gases flows to a reducing valve 34 which is interposed in the gas supply duct 3 between the two active 3/2-way valves 1 and 33. From the outlet of the reducing valve 34 the gas gets to the connection 4 of the active 3/2-way valve 1. As a further active 3/2-way valve 33, suitably an electropneumatically controlled 3/2-way valve (whose switch symbol is used in FIG. 7 for the valve 33) may be used, since it is not operated with as high frequencies as the first active 3/2-way valve 1.

Furthermore it is advantageous to install a reducing valve 34 with adjustable initial pressure. The switching symbol for a valve of this type has been used in FIG. 7. An electronic controlling member 35 serves for allowing the switch-over of the further active 3/2-way valve 33 from the inlet 4' to the inlet 5' and vice-versa only in the switching position I of the first active 3/2-way valve 1—i.e. if the valves 33 and 34 are not flowed through.

What I claim is:

1. In an apparatus for treating the lungs of humans or animals including a source of pressure gas, a gas supply duct having one end having means adapted to be connected to said source and an opposite end having means adapted to be connected to a site of application, valve means in said gas supply duct, and means for actuating said valve means to open and close with frequencies of from 1 to 20 Hz for forming pressure shocks in said gas supply duct in a region of from 0.1 to 5 bar, the improvement which is characterized in said valve means comprises an active 3/2-way valve interposed in the gas supply duct and a passive 3/2-way rapid deaerating valve provided in the gas supply duct between the active 3/2-way valve and the site of application, said active 3/2-way valve having an inlet port connected to said duct leading from said source, an outlet port connected to said duct leading to said deaerating valve and an inlet/outlet port adapted to be connected to either a lower pressure source or to surrounding atmosphere, the passive 3/2-way rapid deaerating valve having an inlet port connected to said duct leading from said active 3/2-way valve, an outlet port connected to said duct leading to said site of application and an inlet/outlet port, a pressure vessel connected to said inlet/outlet port, said passive 3/2-way valve also having valve means comprising a sealing body movable to and fro between two valves seats communicating with said inlet and outlet ports, respectively, whereby the passive 3/2-way rapid deaerating valve is adapted to alternately form a connection between the source of pressure gas and said pressure vessel, or between the pressure vessel and the site of application.

2. An apparatus as set fourth in claim 1, wherein the active 3/2-way valve is a solenoid valve having small flow cross-sections and low moved masses.

3. An apparatus as set fourth in one or both of claims 1 and 2, wherein the passive 3/2-way rapid deaerating valve has larger flow cross-sections as compared to the flow cross-sections of the active 3/2-way valve.

4. An apparatus as set fourth in claim 1 further including a humidifying device disposed between said passive 3/2-way rapid deaerating valve and the site of application the humidifying devise comprising a suction pipe in flow communication with the duct, a capillary tube and a tank for containing a humidifying liquid, the capillary tube sealed relative to the inner wall of the suction pipe, wherein the capillary tube enters into the humdifying liquid tank.

5. An apparatus as set fourth in claim 1, further including a pressure sensor and an electronic controlling element, the pressure sensor being installed in the pressure vessel, the electronic controlling element conductively connecting the pressure sensor to the active 3/2-way valve.

6. An apparatus as set forth in claim 5, wherein the electronic controlling element includes a microprocessor for exactly regulating the switch-over time of the active 3/2-way valve taking into consideration a pressure increase variable in dependence on the nominal pressure prevailing in the pressure vessel over a constant span of time between pressure detection by the pressure sensor and response of the two 3/2-way valves.

7. An apparatus as set fourth in claim 5, wherein a piezo-electic pressure transformer is installed as the pressure sensor.

8. An apparatus as set fourth in claim 1, further including a second source of gas, a reducing valve and a further active 3/2-way valve, the further active 3/2-way valve being provided between the second source of gas and the active 3/2-way valve the reducing valve being interposed between the two active 3/2-way valves, the further active 3/2-way valve having two inlets each connected to a source of pressure gas.

9. An apparatus as set fourth in claim 8, characterized in that an electronic controlling member is provided to electrically interconnect the two active 3/2-way valves, the electronic controlling member being adapted to allow a switch-over of the further active 3/2-way valve only as long as the first active 3/2-way valve interrupts the gas flow from the reducing valve.

10. An apparatus for supplying gas pressure shocks to the lungs of a mammal at a frequency of from 1 to 20 Hertz and a pressure of from 0.1 to 5 bar which includes a gas source and a gass supply duct connected thereto and leading therefrom to a mammel application site wherein the pressure shocks are provided by a system communicating with the gas supply duct, the system comrpising a pressure vessel, a low-pressure retaining vessel, selectively actuated first valve means in said gas supply duct which can allow gas to flow from the gas source along the gas supply duct, a second valve means in said gas supply duct downstream of said first valve means, the second valve means alternating between a primary and secondary position, when in the primary position providing gaseous access from the first valve means to said pressure vessel and when in the secondary position providing gaseous access from the pressure vessel to the mammal application site, the position of said second valve means being directly controlled by the selective actuation of said first valve means, wherein when said first valve means is actuated, gas is allowed to flow from said source along said gas supply duct to switch the second valve means to its primary position, and when said first valve is de-actuated gas flows from said gas supply duct to the low-pressure retaining vessel thereby switching said second valve to its secondary position.

11. The apparatus of claim 10 further including a plurality of sources of pressure gas and means for selectively providing gas supply from one of these various sources.

* * * * *